(12) United States Patent
Siemiarczuk et al.

(10) Patent No.: US 7,733,470 B2
(45) Date of Patent: Jun. 8, 2010

(54) METHOD AND APPARATUS FOR REAL-TIME MEASUREMENT AND CALCULATION OF A FLUORESCENT LIFETIME

(75) Inventors: Aleksander Siemiarczuk, London (CA); Jens Wulf, Locham-Grafelfing (DE)

(73) Assignee: Photon Technology International, Inc., Birmingham, NJ (US)

( * ) Notice: Subject to any disclaimer, the term of this patent is extended or adjusted under 35 U.S.C. 154(b) by 147 days.

(21) Appl. No.: 12/146,893

(22) Filed: Jun. 26, 2008

(65) Prior Publication Data

US 2009/0002691 A1      Jan. 1, 2009

Related U.S. Application Data

(60) Provisional application No. 60/946,154, filed on Jun. 26, 2007.

(51) Int. Cl.
*G01J 1/00* (2006.01)
*G01J 1/53* (2006.01)
*G01N 21/64* (2006.01)
*A61B 6/00* (2006.01)

(52) U.S. Cl. .............. 356/213; 356/318; 250/458.1; 250/459.1; 600/407; 600/477; 436/526

(58) Field of Classification Search .......... 356/213, 356/229, 318, 407–409; 250/458.1, 459.1, 250/416.2; 600/407, 477; 435/287.2; 436/526
See application file for complete search history.

(56) References Cited

U.S. PATENT DOCUMENTS

| | | | | |
|---|---|---|---|---|
| 4,855,930 A * | 8/1989 | Chao et al. | .................... | 702/32 |
| 5,039,219 A * | 8/1991 | James et al. | ................. | 356/318 |
| 5,504,337 A * | 4/1996 | Lakowicz et al. | ......... | 250/461.2 |
| 5,548,124 A * | 8/1996 | Takeshima et al. | ........ | 250/458.1 |
| 5,851,488 A * | 12/1998 | Saul et al. | ..................... | 422/67 |
| 6,272,376 B1 * | 8/2001 | Marcu et al. | ................. | 600/477 |
| 6,890,485 B1 * | 5/2005 | Stylli et al. | .................... | 506/39 |
| 7,015,484 B2 * | 3/2006 | Gillispie et al. | .......... | 250/458.1 |
| 7,183,066 B2 * | 2/2007 | Fernandez-Salas et al. | . | 435/7.32 |
| 2006/0008924 A1 * | 1/2006 | Anker et al. | ................. | 436/526 |
| 2007/0197894 A1 * | 8/2007 | Jo et al. | ...................... | 600/407 |

* cited by examiner

*Primary Examiner*—Sang Nguyen
(74) *Attorney, Agent, or Firm*—Fox Rothschild LLP; Richard C. Woodbridge; Perry M. Fonseca

(57) ABSTRACT

The invention comprises a real-time stroboscopic acquisition protocol for a measurement of the fluorescence decay and a method and apparatus for real-time calculation of the fluorescence lifetime from that measurement.

12 Claims, 5 Drawing Sheets

METHOD AND APPARATUS FOR REAL-TIME MEASUREMENT AND CALCULATION OF A FLUORESCENT LIFETIME

CROSS-REFERENCE TO RELATED APPLICATIONS

This application based on and claims priority to U.S. Provisional Application No. 60/946,154, filed Jun. 26, 2007, which is incorporated fully herein by reference.

BACKGROUND OF THE INVENTION

1. Field of the Invention

This invention relates to real-time measurement and calculation of a fluorescence lifetime.

2. Description of Related Art

Fluorescence lifetime measurement has become a significant analytical tool with clinical applications (U.S. Pat. No. 7,127,282), research applications (U.S. Pat. No. 7,183,066), and process control applications (U.S. Pat. No. 6,890,485). In all of these applications changes in the analyte are detected as changes in the measured fluorescence lifetime.

Three types of experimental methods are used in measuring fluorescent lifetimes; time correlated single photon counting, multi-phase measurement, and the stroboscopic method. (Lakowicz 1991). All of these methods can output a fluorescence decay curve. That curve is a convolution of the instrumental response function and the analyte fluorescence decay. U.S. Pat. No. 5,039,219 provides details of the stroboscopic measurement method.

U.S. Pat. No. 4,855,930, "Method and apparatus for improved time-resolved fluorescence spectroscopy" is typical of the state of the art for calculating the fluorescence lifetime from the fluorescence decay curve. This method uses convolution/deconvolution with least squares minimization. In practice, the method requires acquiring many time points on the fluorescence decay curve and performing minutes of calculation to calculate a lifetime.

SUMMARY OF THE INVENTION

Briefly described, the invention comprises a real-time stroboscopic acquisition protocol for a measurement of the fluorescence decay and a method and apparatus for real-time calculation of the fluorescence lifetime from that measurement. The measurement protocol alternately measures the fluorescence at two pre-defined time delays. The time delays are pre-selected to provide good signal while spanning a significant fraction of the fluorescence decay curve. The calculation method uses these two measurements and the pre-determined instrumental response function to rapidly derive the lifetime.

In one preferred embodiment, the invention includes a method and computer-readable storage media storing computer executable instructions for a method for determining the fluorescent lifetime of a sample in real-time using a stroboscopic instrument. The method includes measuring the instrument response function and pre-scans the decay curve. The method further includes identifying a peak intensity (Ip) of the decay curve and a peak time (Tp) at which the peak intensity occurs, determining a first delay time (Ta) and a second delay time (Tb), measuring a first intensity (Ia) at the first delay time, measuring a second intensity (Ib) at the second delay time and calculating the fluorescent lifetime (T) of the sample in real-time based on the first and second delay times.

The first delay time is determined by scanning the decay curve starting at the peak time (Tp) until the intensity is less than (0.95*Ip) and the second delay time (Tb) is determined by scanning the decay curve starting at the peak time (Tp) until the intensity is less than (0.10*Ip). The calculating of the fluorescent lifetime includes setting a comparison time parameter, 10 nanoseconds for example, and determining whether difference between the peak time and the first delay time is greater than the comparison time parameter. If the difference between the peak time and the first delay time is greater than the comparison time parameter, the fluorescent lifetime (T) is calculated according to the equation $$T=(Tb-Ta)/\ln(Ib/(Ia)).$$

When the difference between the peak time and the first delay time is greater than the comparison time parameter, an old fluorescent lifetime (To) is calculated according to the equation $$To = (Ta - Tb)/\ln(Ib/(Ia*(1+r))),$$

where $$r = \frac{\int_{Ta}^{Tb} L(t)\exp(t/T)dt}{\int_0^{Ta} L(t)\exp(t/T)dt}.$$

The new lifetime (Tn) is then calculated according to the equation $$Tn=(Ta-Tb)/\ln(Ib/(Ia*(1+r))).$$

These calculations are repeating until the absolute value of (To−Tn) is less than (0.001*Tn), at which point the fluorescent lifetime (T) is set to be equal to the new lifetime (Tn).

DETAILED DESCRIPTION OF THE PREFERRED EMBODIMENT

The methods and apparatus disclosed herein advantageously improve the state of the art in that the stroboscopic measurements and calculations for determining the fluorescent lifetime can be performed many times per second. Faster measurement reduces risk in clinical measurements, increases throughput in research applications, and improves response time in process control. Faster measurement enhances the use of fluorescent lifetime measurement in kinetics studies such as stop-flow and in parametric studies such observing protein conformal changes with temperature.

Exemplary embodiments of a real-time fluorescence lifetime measurement method and apparatus according to the present invention are explained below in detail with reference to the accompanying drawings.

Figure 1:
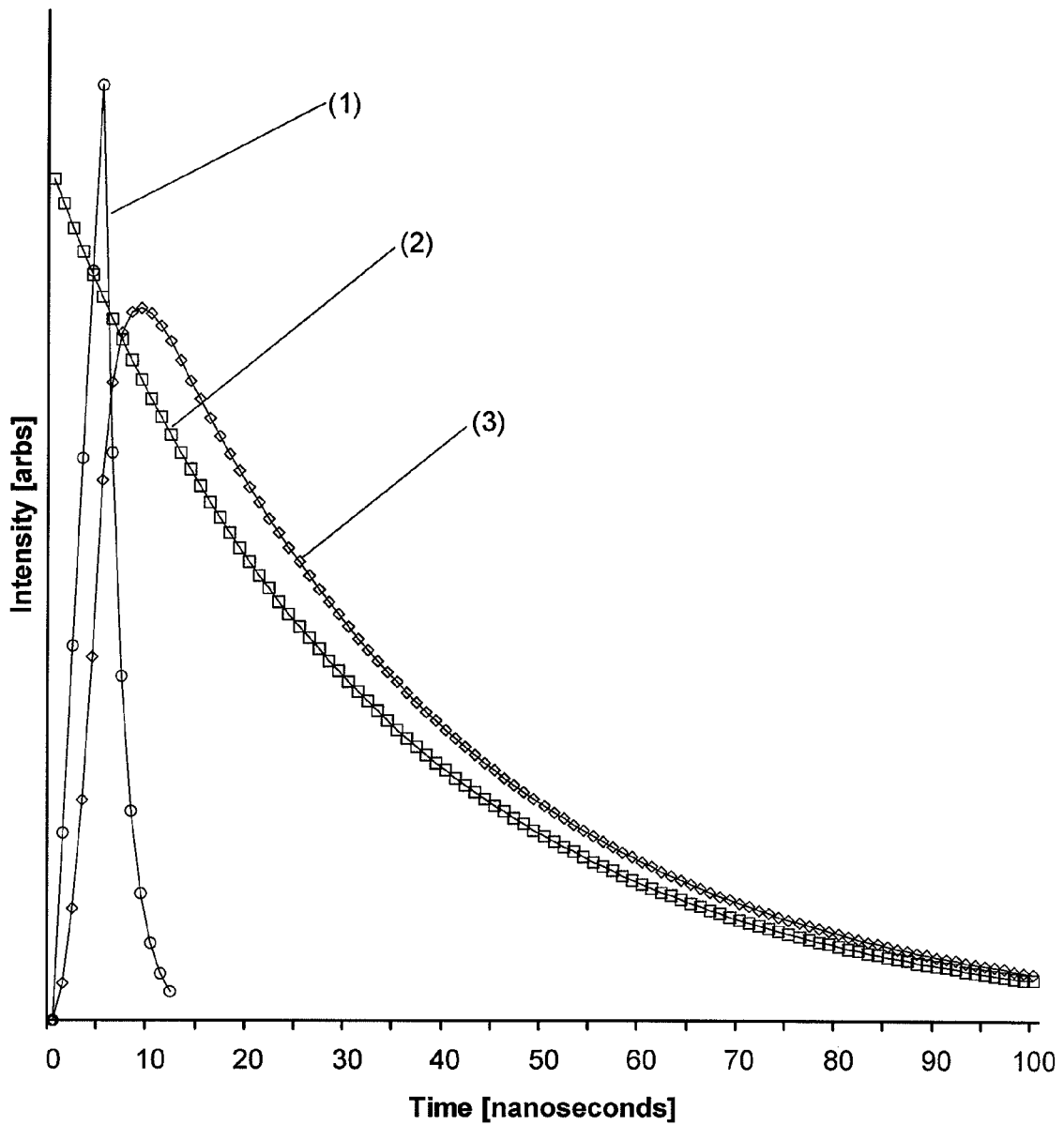
FIG. 1 shows an instrumental response function, a fluorescent decay, and the resulting measured decay curve.

FIG. 1 shows for reference an instrumental response function, L(t), (1), a fluorescent decay, F(t), (2), and the resulting measured decay curve, D(t), (3). The detection system in the stroboscopic instrument observes a fluorescent decay curve (2) response function associated with each excitation of a fluorescent molecule. (Details of the stroboscopic instrument are given in U.S. Pat. No. 5,039,219.) If the fluorescent decay were instantaneous, the instrument would not record an infinitely sharp signal, but would record the instrument response function (1). The instrument response function results because the stroboscopic instrument provides excitation light with a finite pulse width and detects the fluorescence with a finite response speed. The measured decay curve (3) is the convolution of the instrument response function (1) and the fluorescent decay (2).

Figure 2:
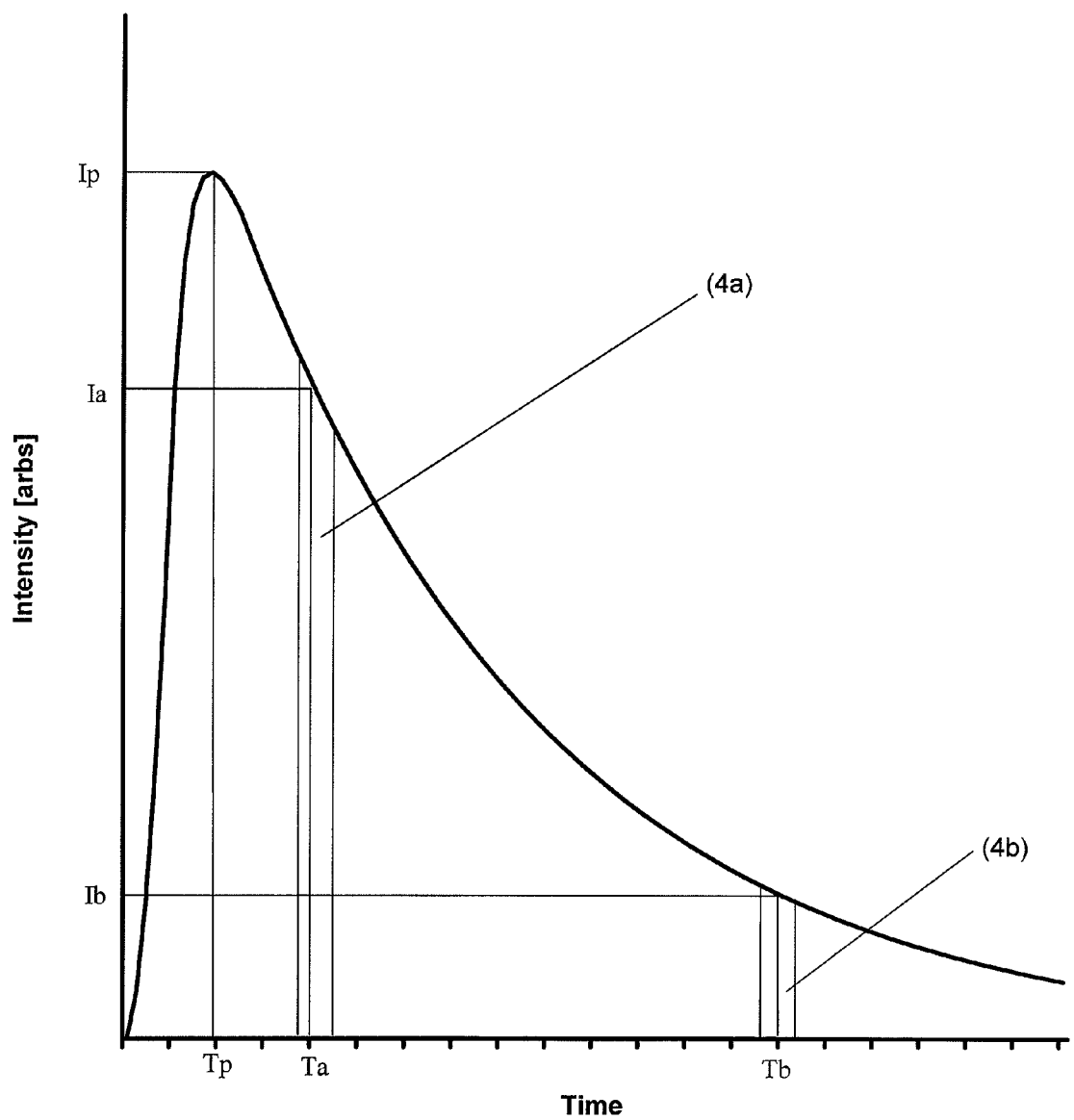
FIG. 2 shows two measurement windows in a stroboscopic measurement of fluorescence.

FIG. 2 shows two time windows, (4a) and (4b), centered at times, Ta and Tb, respectively in which the stroboscopic system acquires fluorescent signals of average intensity, Ia, and Ib, respectively. The peak signal (5) has been labeled (tp, Ip) for reference.

Figure 3:
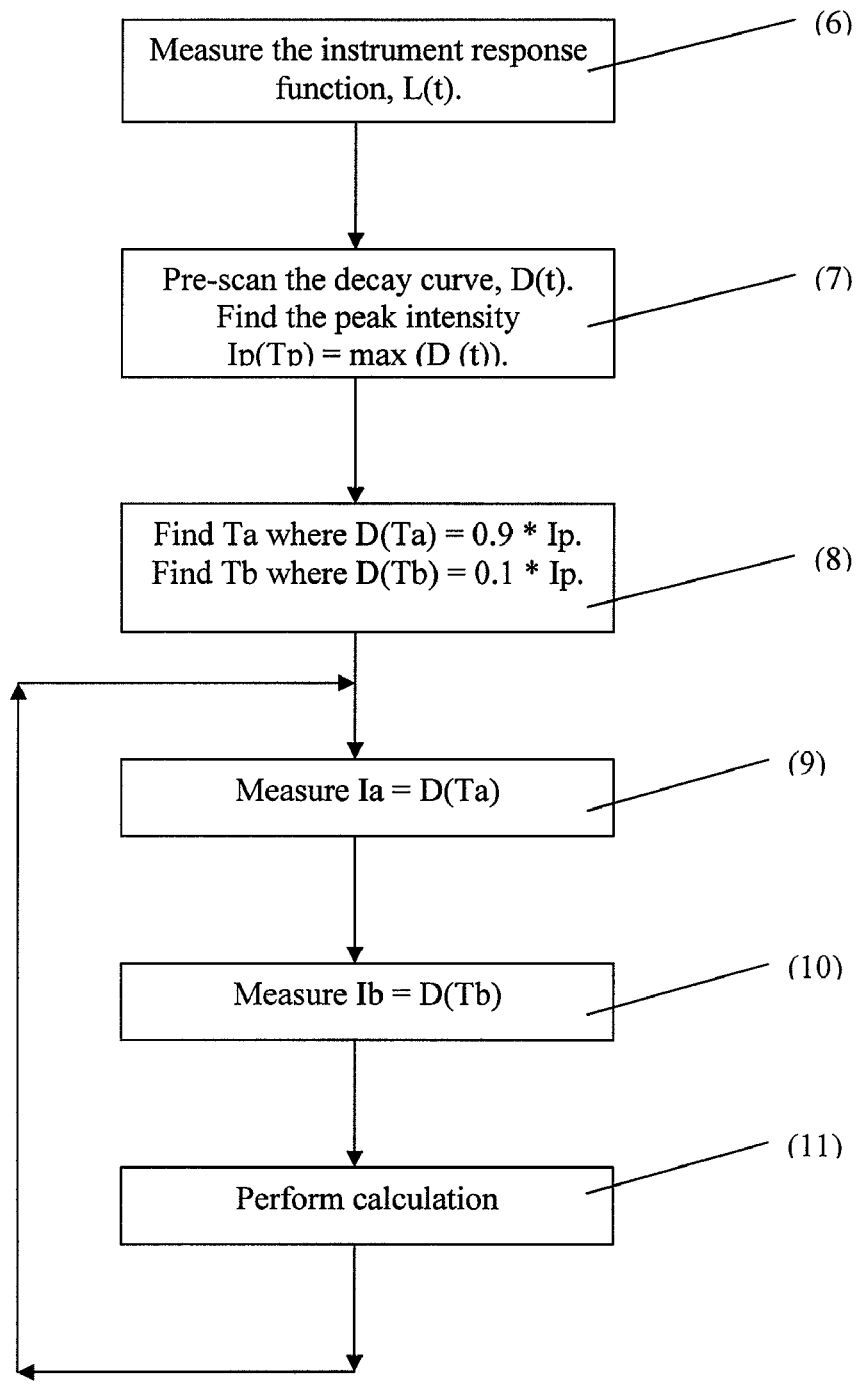
FIG. 3 shows the series of steps in the real-time stroboscopic acquisition protocol for producing data suitable for real-time fluorescent lifetime measurement.

FIG. 3 shows a series of steps for performing the measurement protocol. Normally, these steps are executed as a computer program.

In step (6) the instrument response function of the stroboscopic instrument, L(t), (1) is determined. In many instruments this determination is a one-time event that may be determined to high precision through repeated measurement. Details of this procedure are provided in U.S. Pat. No. 5,039,219.

In step (7) a pre-scan over the full life-time range of the instrument measures the decay curve, D(t). The peak intensity of the measured decay curve, Ip (Tp) is identified. The range of the pre-scan can be set to another time window by an experienced user if an approximate lifetime value and the temporal position of the instrument response function are known from previous measurements or for similar materials. Because the decay curve, D(t), is dependent on both the material under study and the stroboscopic instrument, the measured instrument response function, L(t), is used to separate the effects of the instrument on the decay curve, D(t), from the intrinsic property of the material under study.

In step (8) values of Ta (4a) and Tb (4b) are determined such that Ia=0.95*Ip and Ib=0.10*Ip. The value Ta is found by scanning the decay curve starting at time tp until I<0.95*Ip. The best value Ta is then found by linear interpolation between that value and the previous time value. The time Tb is found similarly. In practice, the decay fraction parameters, 0.95 and 0.10, may be set to other values by an experienced user.

In step (9) data is acquired at delay Ta.

In step (10) data is acquired at delay Tb.

Figure 4:
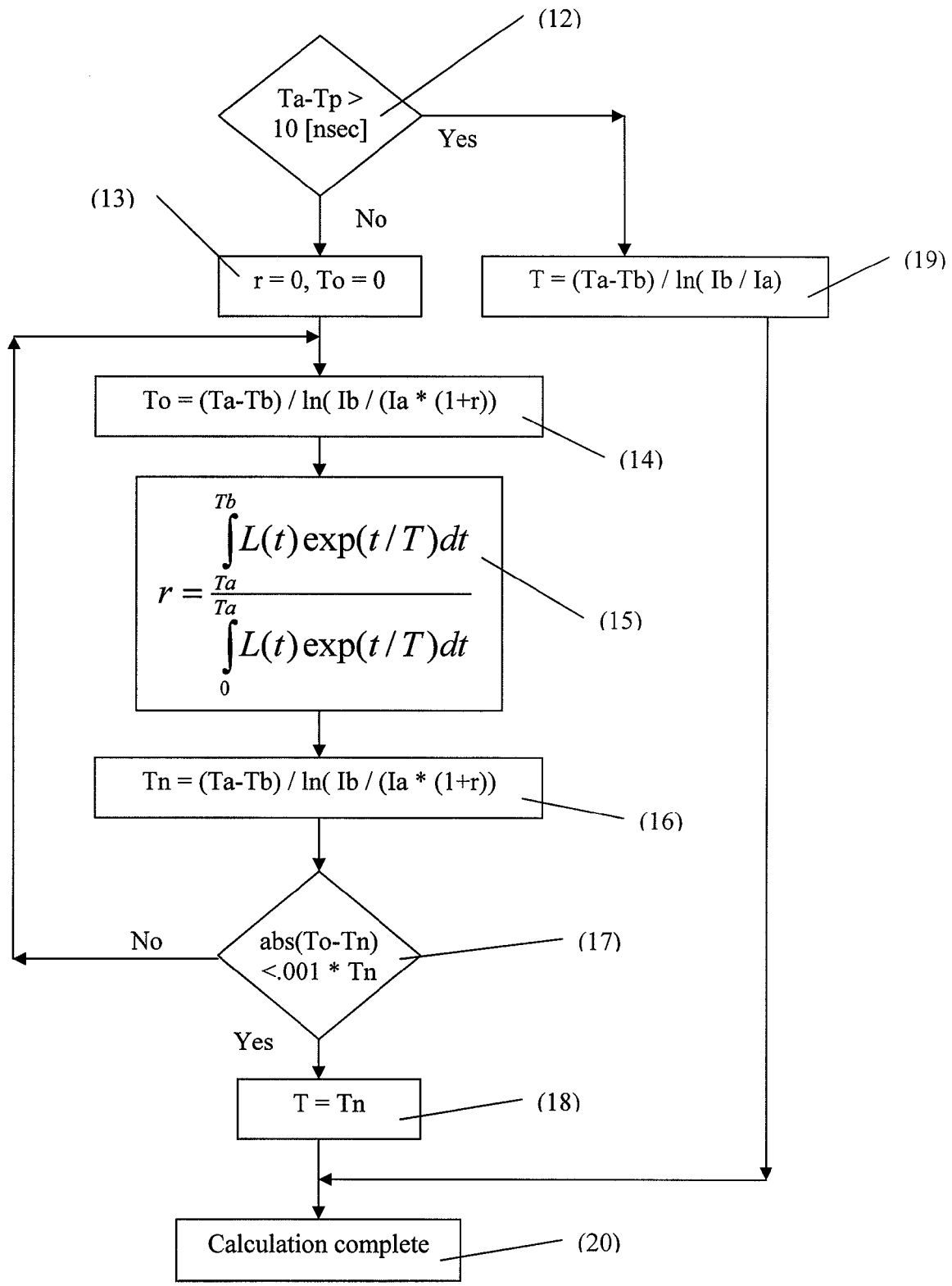
FIG. 4 shows the series of steps in the real-time method of calculating the lifetime from said data.

In step (11), the lifetime is calculated as shown in FIG. 4. The sequence then repeats beginning with step (9).

FIG. 4 shows a series of steps for performing the lifetime calculation. Normally, these steps are executed as a computer program.

In step (12) the value (Ta) is compared to the time at which the peak occurred, Tp. If (Ta−Tp)>10 [nsec] then step (13) is executed. Otherwise step (19) is executed. The comparison parameter, 10 [nsec], may be set to other values by an experienced user.

In step (13) initial values are set, r=0.

In step (14) old lifetime, To, is calculated using $$To=(Ta-Tb)/ln(Ib/(Ia*(1+r)))$$

In step (16) if abs(To−Tn)<0.001*Tn then the calculation is complete. In practice, the convergence parameter, 0.001, may be set to other values by an experienced user.

In step (15) a new value of r is calculated using numerical integration of the equation.

$$r = \frac{\int_{Ta}^{Tb} L(t)\exp(t/T)\,dt}{\int_{0}^{Ta} L(t)\exp(t/T)\,dt}$$

In step (16) new lifetime, Tn, is calculated using $$Tn=(Ta-Tb)/ln(Ib/(Ia*(1+r)))$$

In step (17) if abs(To−Tn)>0.001*Tn then the sequence iterates at step (14). In normal operation the sequence is repeated no more than 6 times before the convergence test (17) is satisfied. The iteration test parameter, 0.001, may be set to another value by an experienced user in order to affect the speed of the convergence, e.g. if the iteration test parameter is set to 0.01 the convergence will be faster than with the convergence test parameter =0.001.

In step (18), the lifetime is set equal to Tn. The calculation is then complete

In step (19) the value of the lifetime is alternatively calculated as $$T=(Ta-Tb)/ln(Ib/(Ia)).$$

The calculation is then complete.

Figure 5:
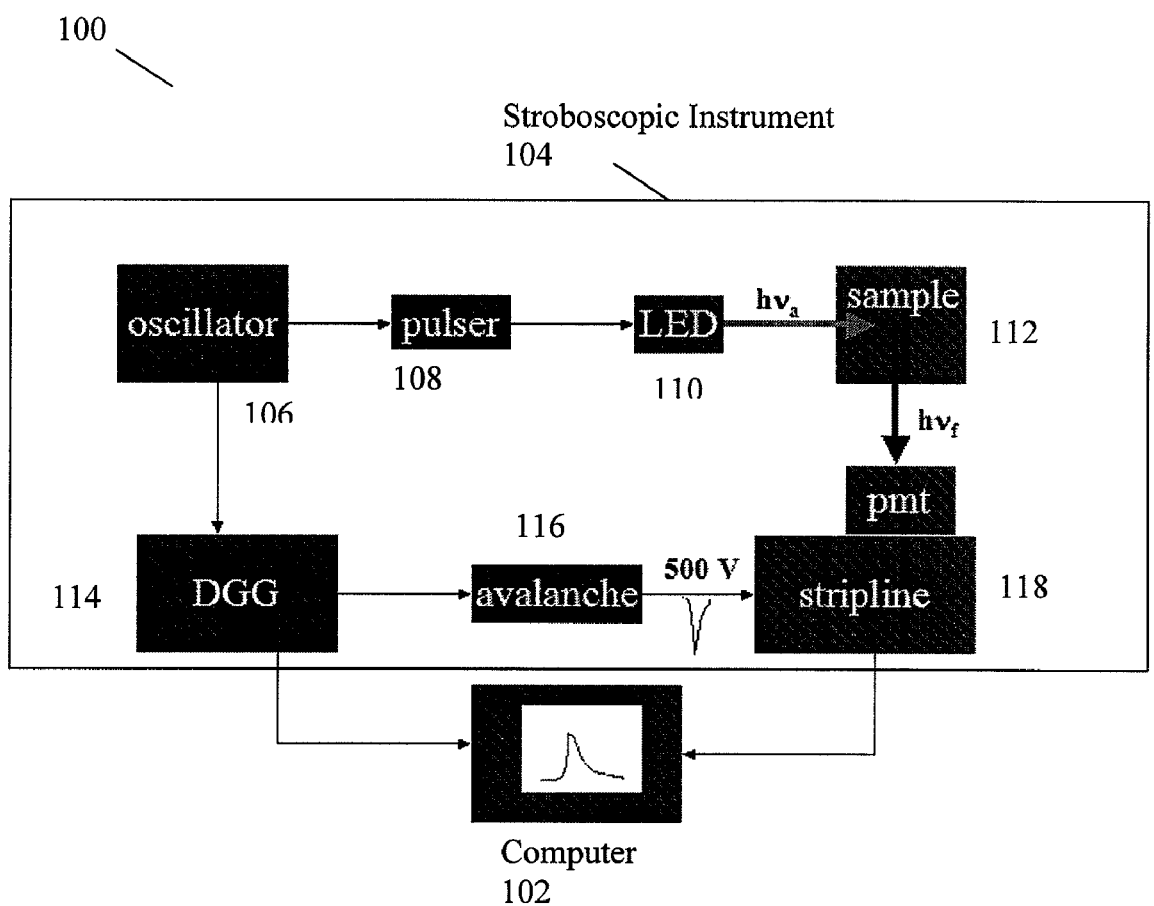
FIG. 5 shows a block diagram of an apparatus for determining the fluorescent lifetime of a sample in real-time.

FIG. 5 shows a block diagram of one preferred embodiment of an apparatus 100 for determining the fluorescent lifetime of a sample 112 in real-time according to the present invention, using an LED-based stroboscopic instrument 104 connected to a computer 102. The stroboscopic instrument 104 includes a master clock oscillator 100 that generates pulses at a 25 kHz frequency. The pulses generated by master clock oscillator 100 are routed simultaneously to an LED pulser 108 and a digital delay gate generator (DGG) unit 114. The LED pulser 108 triggers an LED 110. The LED 110 flashes and excites the sample 112, which subsequently emits fluorescence. In synchronization with the pulses from the LED pulser 108, the pulses generated by master clock oscillator 100 also trigger the DGG unit 114. The DGG unit 114 outputs a delayed transistor-transistor logic (TTL) pulse. The DGG unit 114 is under the control of the computer 102 and the value of the TTL pulse delay is determined by acquisition software in the computer. The delayed pulse from the DGG unit 114 triggers an avalanche circuit 116, which provides a high voltage pulse (for example, about 500 V) which activates detection circuitry within a photomultiplier (PMT)/stripline block 118. The high voltage pulse creates a gain and a temporal discrimination gate for the photomultiplier 118, which detects fluorescence intensity at this given time delay. The time delay is then changed and the intensity is measured at the new time delay and the cycle is repeated as many times as necessary. The computer 102 calculates the fluorescent lifetime (T) of the sample 112 in real-time based on the measured fluorescence intensities.

Elements of the present invention can be realized in hardware, software, or a combination of hardware and software. Any kind of computer system or other apparatus adapted for carrying out the methods described herein is suited. A typical combination of hardware and software could be a general purpose computer system with a computer program that, when being loaded and executed, controls the computer system such that it carries out the methods described herein. Elements of the present invention can also be embedded in a computer program product, which comprises all the features enabling the implementation of the methods described herein, and which—when loaded in a computer system—is able to carry out these methods.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method for determining the fluorescent lifetime of a sample in real-time using a stroboscopic instrument, the method comprising the steps of:
   measuring the instrument response function;
   pre-scanning the decay curve;
   identifying a peak intensity (Ip) of the decay curve and a peak time (Tp) at which the peak intensity occurs;
   determining a first delay time (Ta) and a second delay time (Tb);
   measuring a first intensity (Ia) at the first delay time;
   measuring a second intensity (Ib) at the second delay time; and
   calculating the fluorescent lifetime (T) of the sample in real-time based on the first and second delay times and the corresponding intensities,
   wherein the step of calculating the fluorescent lifetime (T) comprise the steps of:
      setting a comparison time parameter;
      determining whether the difference between the peak time and the first delay time is greater than the comparison time parameter; and
      if the difference between the peak time and the first delay time is greater than the comparison time parameter, calculating the fluorescent lifetime (T) according to the equation $T=(Ta-Tb)/ln(Ib)/(Ia)$.

2. The method according to claim 1, wherein calculating the fluorescent lifetime further comprises the steps of:
   comparing the peak time and the first delay time, when the difference between the peak time and the first delay time is greater than the comparison time parameter,
   calculating an old fluorescent lifetime (To) according to the equation:

$To=(Ta-Tb)/ln(Ib/(Ia*(1+r)))$;

calculating r according to the equation:

$$r = \frac{\int_{Ta}^{Tb} L(t)\exp(t/T)\,dt}{\int_{0}^{Ta} L(t)\exp(t/T)\,dt};$$

calculating a new lifetime (Tn) according to the equation:

$Tn=(Ta-Tb)/ln(Ib/(Ia*(I+r)))$;

repeating the comparing, calculating of r, and calculating of a new lifetime steps until the absolute value of (To−Tn) is less than (0.001*Tn); and
   setting the fluorescent lifetime (T) equal to the new lifetime (Tn).

3. The method according to claim 1, wherein the comparison time parameter is 10 nanoseconds.

4. A computer-readable storage media storing computer executable instructions for a method of determining the fluorescent lifetime of a sample in real-time using a stroboscopic instrument, the method comprising the steps of:
   measuring the instrument response function;
   pre-scanning the decay curve;
   identifying a peak intensity (Ip) of the decay curve and a peak time (Tp) at which the peak intensity occurs;
   determining a first delay time (Ta) and a second delay time (Tb);
   measuring a first intensity (Ia) at the first delay time; measuring a second intensity (Ib) at the second delay time; and
   calculating the fluorescent lifetime (T) of the sample in real-time,
   wherein the step of calculating the fluorescent lifetime (T) further comprises the steps of:
      setting a comparison time parameter;
      determining whether difference between the peak time and the first delay time is greater than the comparison time parameter; and
      if the difference between the peak time and the first delay time is greater than the comparison time parameter, calculating the fluorescent lifetime (T) according to the equation $T=(Ta-Tb)/ln(Ib/(Ia)$.

5. The computer-readable storage media according to claim 4, wherein the method of calculating the fluorescent lifetime further comprises the steps of:
   calculating, if the difference between the peak time and the first delay time is greater than the comparison time parameter, an old fluorescent lifetime (To) according to the equation $To=(Ta-Tb)/ln(Ib/(Ia*(1+r)))$;

calculating r according to the equation:

$$r = \frac{\int_{Ta}^{Tb} L(t)\exp(t/T)\,dt}{\int_{0}^{Ta} L(t)\exp(t/T)\,dt};$$

calculating a new lifetime (Tn) according to the equation:

$Tn=(Ta-Tb)/ln(Ib/(Ia*(I+r)))$;

repeating the comparing, calculating of r, and calculating of a new lifetime steps until the absolute value of (To−Tn) is less than (0.001*Tn); and
   setting the fluorescent lifetime (T) equal to the new lifetime (Tn).

6. The computer-readable storage media according to claim 4, wherein the method of calculating the fluorescent lifetime uses a comparison time parameter of 10 nanoseconds.

7. An apparatus for determining the fluorescent lifetime of a sample in real-time using a stroboscopic instrument, said apparatus comprising:
   means for measuring the instrument response function;
   means for pre-scanning the decay curve;

means for identifying a peak intensity (Ip) of the decay curve and a peak time (Tp) at which the peak intensity occurs; means for determining a first delay time (Ta) and a second delay time (Tb);

means for measuring a first intensity (Ia) at the first delay time;

means for measuring a second intensity (Ib) at the second delay time; and means for calculating the fluorescent lifetime (T) of the sample in real-time sample in real-time based on the first and second delay times and the corresponding intensities, wherein said means for calculating the fluorescent lifetime (T) further comprises:

means for setting a comparison time parameter;

means for determining whether the difference between the peak time and the first delay time is greater than the comparison time parameter; and means for, if the difference between the peak time and the first delay time is greater than the comparison time parameter, calculating the fluorescent lifetime (T) according to the equation $T=(Ta-Tb)/ln(Ib/(Ia)$.

8. The apparatus according to claim 7, wherein calculating the fluorescent lifetime further comprises:

means for calculating, if the difference between the peak time and the first delay time is greater than the comparison time parameter, an old fluorescent lifetime (To) according to the equation:

$To=(Ta-Tb)/ln(Ib/(Ia*(1+r)))$;

means for calculating r according to the equation:

$$r = \frac{\int_{Ta}^{Tb} L(t)\exp(t/T)\,dt}{\int_{0}^{Ta} L(t)\exp(t/T)\,dt};$$

means for calculating a new lifetime (Tn) according to the equation:

$Tn=(Ta-Tb)/ln(Ib/(Ia*(1+r)))$ means for repeating the comparing, calculating of r, and calculating of a new lifetime steps until the absolute value of (To−Tn) is less than (0.001*Tn); and means for setting the fluorescent lifetime (T) equal to the new lifetime (Tn).

9. The apparatus according to claim 7, wherein the comparison time parameter is 10 nanoseconds.

10. A method for determining the fluorescent lifetime of a sample in real-time using a stroboscopic instrument, the method comprising the steps of:

measuring the instrument response function;

pre-scanning the decay curve;

identifying a peak intensity (Ip) of the decay curve and a peak time (Tp) at which the peak intensity occurs;

determining a first time delay (Ta) and a second time delay (Tb);

measuring a first intensity (Ia) at the first delay time;

measuring a second intensity (Ib) at the second delay time; and calculating the fluorescent lifetime (T) of the sample in real-time based on the first (Ta) and second (Tb) delay times and the corresponding intensities, wherein the first delay time (Ta) is determined by scanning the decay curve starting at the peak time (Tp) until the intensity is less than (0.95*Ip), and the second delay time (Tb) is determined by scanning the decay curve starting at the peak time (Tp) until the intensity is less than (0.10*Ip).

11. A computer-readable storage media storing computer executable instructions for a method of determining the fluorescent lifetime of a sample in real-time using a stroboscopic instrument, the method comprising the steps of:

measuring the instrument response function;

pre-scanning the decay curve;

identifying a peak intensity (Ip) of the decay curve and a peak time (Tp) at which the peak intensity occurs;

determining a first time delay (Ta) and a second time delay (Tb);

measuring a first intensity (Ia) at the first delay time;

measuring a second intensity (Ib) at the second delay time; and calculating the fluorescent lifetime (T) of the sample in real-time based on the first (Ta) and second (Tb) delay times and the corresponding intensities, wherein the first delay time (Ta) is determined by scanning the decay curve starting at the peak time (Tp) until the intensity is less than (0.95*Ip), and the second delay time (Tb) is determined by scanning the decay curve starting at the peak time (Tp) until the intensity is less than (0.10*Ip).

12. An apparatus for determining the fluorescent lifetime of a sample in real-time using a stroboscopic instrument, said apparatus comprising:

means for measuring the instrument response function;

means for prerscanning the decay curve;

means for identifying a peak intensity (Ip) of the decay curve and a peak time (Tp) at which the peak intensity occurs;

means for determining a first delay time (Ta) and a second delay time (Tb);

means for measuring a first intensity (Ia) at the first delay time;

means for measuring a second intensity (Ib) at the second delay time; and means for calculating the fluorescent lifetime (T) of the sample in real-time based on the first and second delay times and the corresponding intensities;

wherein the first delay time is determined by scanning the decay curve starting at the peak time (Tp) until the intensity is less than (0.95*Ip) and the second delay time (Tb) is determined by scanning the decay curve starting at the peak time (Tp) until the intensity is less than (0.10*Ip).

* * * * *